United States Patent [19]

West

[11] Patent Number: 4,602,944
[45] Date of Patent: Jul. 29, 1986

[54] HERBICIDAL PYRIDINIUM COMPOUNDS AND COMPOSITIONS
[75] Inventor: Peter J. West, Great Shelford, England
[73] Assignee: FBC Limited, England
[21] Appl. No.: 654,909
[22] Filed: Sep. 27, 1984
[30] Foreign Application Priority Data Oct. 14, 1983 [GB] United Kingdom ............... 8327658

[51] Int. Cl.[4] .................. C07D 213/75; C07D 213/89; A01N 43/40
[52] U.S. Cl. ........................ 71/94; 546/262; 546/291; 546/292; 546/276; 548/268; 71/92
[58] Field of Search ........................ 546/291, 262, 292; 71/94

[56] References Cited

U.S. PATENT DOCUMENTS 4,013,669 3/1977 Parsons ............... 546/269

FOREIGN PATENT DOCUMENTS 0024259 2/1981 European Pat. Off. ............... 71/94
2056438 3/1981 United Kingdom ............... 71/94

Primary Examiner—Alan L. Rotman
Attorney, Agent, or Firm—Lawrence Rosen

[57] ABSTRACT

Herbicidally-active compounds of the formula:

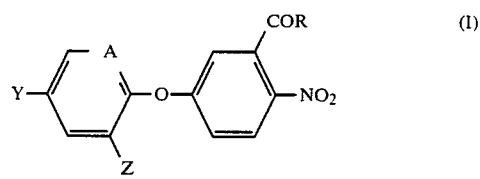

where:
Y represents halo or trifluoromethyl;
Z represents hydrogen, halo, trifluoromethyl or nitro;
A represents —N= or

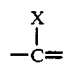

where X is as defined above for Z; and
R represents —N⁻Q⁺ or —NH—Q⁺An⁻ where Q⁺ is a quaternized heterocyclic group bonded through a nitrogen atom thereof, and An⁻ is a suitable anion, methods for their preparation and compositions containing them.

14 Claims, No Drawings

HERBICIDAL PYRIDINIUM COMPOUNDS AND COMPOSITIONS

This invention concerns herbicidally active compounds, processes for their preparation and compositions containing them.

In one aspect the invention provides the compounds of the formula:

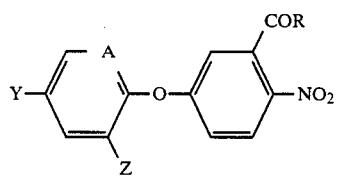

where:
Y represents halo or trifluoromethyl;
Z represents hydrogen, halo, trifluoromethyl or nitro;
A represents —N= or

where X is as defined above for Z; and
R represents —N⁻Q⁺ or —NH—Q⁺An⁻ where Q⁺ is a quaternised heterocyclic group bonded through a nitrogen atom thereof, and An⁻ is a suitable anion.

When X, Y or Z represents halo, it is preferably chloro.

X and Z and desirably different from each other.

One of X and Z, but not both, preferably represents hydrogen.

The quaternised heterocyclic group which Q represents is preferably a 5- or 6-membered unsaturated group, which may if desired contain one or more heteroatoms besides the nitrogen atom through which it is bonded to the remainder of the molecule. Such heteroatoms, if present, are preferably nitrogen, oxygen or sulphur atoms, particularly nitrogen atoms. Specific examples of preferred heterocyclic groups include pyrdinium and triazolium.

The heterocyclic group which Q represents may be unsubstituted or may be substituted by one or more groups such as alkyl (especially of 1 to 4 carbon atoms, e.g. methyl, ethyl, n-propyl, isopropyl, n-butyl or t-butyl), alkenyl (especially of 2 to 6 carbon atoms, e.g. allyl), aryl (especially phenyl), aralkyl (especially phenylalkyl of 7 to 10 carbon atoms, e.g. benzyl), halogen (especially chlorine or bromine), alkoxy (especially of 1 to 4 carbon atoms, e.g. methoxy or ethoxy) or alkoxycarbonyl (especially of 2 to 6 carbon atoms, e.g. methoxycarbonyl). Substituents on two adjacent positions may together form a further ring.

An⁻ may be any suitable anion, for example chloride, bromide, iodide or methylsulphate. The exact identity of the anion is not of great importance, however, since the activity of the compounds of formula I is believed to reside in the cationic portion thereof. In general, the anion will only add its own intrinsic activity, if any.

In a particularly preferred group of compounds of formula I, Y represents a trifluoromethyl, Z represents chloro, A represents —CH=, and R represents —N⁻Q⁺ where Q⁺ represents pyridinium-1-yl which may be substituted on one or more of its carbon atoms or 1,2,4-triazolium-4-yl which is substituted on the 1-position by methyl, ethyl, allyl or benzyl, but which is preferably unsubstituted pyridinium-1-yl.

Specific preferred compounds according to the invention include:
1-[5-(2-chloro-4-trifluoromethylphenoxy)-2-nitrobenzamido]pyridinium chloride;
1-[5-(2-chloro-4-trifluoromethylphenoxy)-2-nitrobenzamido]pyridinium internal salt;
5-(2-chloro-4-trifluoromethylphenoxy)-N-(4-ethyl-1-pyridinio)-2-nitrobenzamidate;
and those of the Examples provided hereinafter.

In another aspect the invention provides a process for the preparation of a compound of formula I where R represents —NH—Q⁺An⁻ in which an acyl halide of the formula:

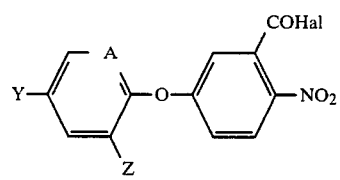

where Y, Z and A are as defined hereinbefore and Hal represents a halogen atom, is reacted with a compound of formula H₂N—Q⁺An⁻ where Q⁺ and An⁻ are as defined hereinbefore, to give the desired compound.

The reaction is conveniently effected in a solvent which is inert under the reaction conditions employed, e.g. acetonitrile, and with heating, e.g. to reflux.

The compounds of formula II are either known compounds or may be prepared by methods known per se from the corresponding carboxylic acids by reaction with thionyl chloride. The carboxylic acid starting materials may themselves be prepared by methods which are analogous to those employed for the preparation of similar known compounds.

The compounds of formula H₂N—Q⁺An⁻ are either known compounds or may be prepared by methods known per se.

The compounds of formula I where R represents —N⁻Q⁺ may be prepared from the corresponding compounds of formula I where R represents —NH—Q⁺An⁻ by reaction thereof with a base, especially a strong base, e.g. a hydroxide or alkoxide such as sodium hydroxide or sodium methoxide.

The compounds of formula I are herbicidally active. In particular, they are active against many broadleaf weeds, e.g. morning glory, cocklebur, prickly sida, velvetleaf, jimsonweed, ragweed, black nightshade, fat hen, pale persicaria, redshank, purslane, sicklepod, coffeeweed, green foxtail and lambsquarter. They also possess activity against certain grassy weeds, e.g. blackgrass, Johnsongrass and couchgrass. The compounds are comparatively inactive against certain crop species, notably soybeans, cotton, cereals (e.g. wheat, barley, maize, oats and rye), and peanuts, and may thus be of use as selective herbicides.

In a further aspect, this invention provided a method of combating weeds at a locus infested with or liable to be infested with them, which method comprises applying to said locus a herbicidally-effective amount of one or more compounds of formula I.

The present compounds are normally employed in the form of compositions, which can be prepared by admixing the ingredients. Usually the compositions are initially produced in the form of concentrates, e.g. containing 0.5 to 99%, especially 0.5-85% of the present compounds, and these are diluted with water or hydrocarbon, usually water, for application, generally such that the concentration of the compounds is 0.05-5% by weight.

The compositions normally contain a surface active agent and/or a carrier.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present.

The carrier may be a liquid other than water, for example an organic solvent, such as a water immiscible solvent e.g. a hydrocarbon which boils within the range 130°-270°, in which the compound is dissolved or suspended. A concentrate containing a water immiscible solvent suitably also contains a surface active agent so that the concentrate acts as a self-emulsifiable oil on admixture with water. The liquid may be a water-immiscible solvent e.g. 2-methoxy ethanol, methanol, propylene glycol, diethylene glycol, diethylene glycol monoethyl ether, formamide or methylformamide.

The carrier may be a solid, which may be finely divided. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitable also with a solvent.

A flowable suspension concentrate may be formed by grinding the compound with water, a wetting agent and a suspending agent.

Thus the present composition can for example be solid (e.g. dust or granules) and contain a solid carrier or liquid (e.g. an emulsifiable concentrate) and contain a liquid carrier which is a hydrocarbon which boils within the range 130°-270° C.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters or phosphoric acid with a fatty alcohol ethoxylate or salts of such esters, fatty alcohol suphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulpho-succinates e.g. the sodium sulphonate of dioctyl succinate.

The surface active agents may also comprise nonionic agents, for example condensation products of fatty acid esters, fatty alcohols, fatty acid amides or alkyl-substituted phenols with ethylene oxide, fatty esters or polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

The surface active agents may also comprise cationic agents, for example alkyl- and/or aryl-substituted quaternary ammonium compounds such as cetyl trimethyl-ammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulphosuccinates, alkyl phenol ethoxylates, and fatty alkyl ethoxylates.

The present active compounds and especially those specifically described herein may be admixed with another pesticide, e.g. herbicide, insecticide or fungicide, or with a plant growth regulant or with a fertilizer. Particular advantages are obtained with mixtures with a second herbicide. The present compounds may be used sequentially with a second herbicide, e.g. one herbicide applied before planting or before emergence of a crop and the other herbicide applied after emergence of the crop.

The second herbicide employed in admixture or sequentially with the compounds of the present invention may be, for example, a substituted benzofuran herbicide, a phenoxyaliphatic acid, substituted urea, triazine, phenol, nitrile, bipyridylium compound, substituted benzoic acid, halogenated aliphatic acid, carbamate, thiocarbamate, chloroacetamide, diazine, arsenic compound or other herbicidal compound. In respect of selective herbicidal compositions for post-emergence use, the second herbicide is preferably a substituted phenoxyaliphatic acid; in respect of selective herbicidal compositions for pre-emergence use, the second herbicide is preferably a substituted benzofuran, a substituted urea or triazine.

Specific preferred admixtures are those of one or more of the compounds specifically described herein with one or more of naptalam, chloramben, triallate, bentazone, acifluorfen, barban, chlorpropham, dinitramine, chlorthal-dimethyl, dalapon, diphenamid, DNBP, benazolin, metolachlor, alachlor, metribuzin, linuron, chlorbromuron, paraquat, pendimethalin, propachlor, glyphosate, metribuzin, sodium chlorate, oryzalin, chloroxuron, profluralin, trifluralin, sulfallate, vernolate, 2,4-DB, oxadiazon or benfluralin.

The ratio of the present compound to the second pesticide may vary over a wide range according to the particular compounds involved and the intended use. In general the ratio of present compound to second pesticide lies in the range 1:99 to 99:1, preferably 1:0.1 to 1:15, more preferably 1:0.2 to 5:1, and especially 1:0.3 to 3:1.

The present compounds may be in admixture with non-phytotoxic oils, e.g. Agri-Oil Plus or Sun Oil 11E.

The present compounds are usually employed at a rate of from 0.25 to 8 kg per hectare, for example 0.5 to 2 kg per hectare.

The present compounds may be applied to plants, the soil, land or aquatic areas, and especially to a locus at which a crop is growing or is to grow. The compounds may be applied pre- or post-emergence of the crop.

The invention is illustrated by the following Examples.

EXAMPLE 1

1-[5-(2-chloro-4-trifluoromethylphenoxy)-2-nitrobenzamido]pyridinium chloride

1-Aminopyridinium chloride (2.9 g) was added to 5-(2-chloro-4-trifluoromethylphenoxy)-2-nitrobenzoyl chloride (7.6 g) in acetonitrile (50 ml). The mixture was stirred and heated to reflux. After 20 minutes a solid precipitated. Reflux was continued for a further 40 minutes. Then the mixture was cooled in ice and the solid filtered off. The solid was washed with cold acetonitrile, then with ether, and was air dried to give 7.4 g of the desired product, mp 234°–237° C.

EXAMPLE 2

1-[5-(2-chloro-4-trifluoromethylphenoxy)-2-nitrobenzamido]pyridinium internal salt The product of Example 1 (2.7 g) was dissolved in acetone (20 ml) and water (5 ml). A 40% aqueous solution of sodium hydroxide was then added dropwise with stirring until the mixture was alkaline. Water was added to a total volume of 40 ml. and the mixture was left to crystallise. The solid produced was filtered off, washed with water and dried in vacuo to give 2.1 g of the desired product, mp 169°–171° C.

EXAMPLES 3–6

The following compounds of formula I were prepared by methods analogous to that of Example 1:

| Ex No. | Y | Z | A | Q+ | An− | mpt |
|---|---|---|---|---|---|---|
| 3 | CF$_3$ | Cl | —CH= | 2-methyl-pyridinium-1-yl | Cl | 232–235° C. |
| 4 | CF$_3$ | Cl | —CH= | 1-allyl-1,2,4-triazolium-4-yl | Cl | 141–143° C. |
| 5 | CF$_3$ | Cl | —CH= | 1-benzyl-1,2,4-triazolium-4-yl | Cl | 169–172° C. |
| 6 | CF$_3$ | NO$_2$ | —CH= | 1-benzyl-1,2,4-triazolium-4-yl | Cl | 181–184° C. |

EXAMPLES 7–14

The following compounds of formula I were prepared by methods analogous to that of Example 2:

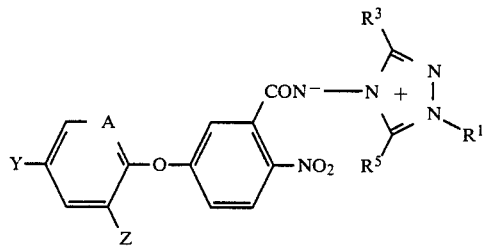

| Ex. No | Y | Z | A | R$^1$ | R$^3$ | R$^5$ | mpt |
|---|---|---|---|---|---|---|---|
| 7 | Cl | Cl | —CH= | benzyl | H | H | 147–148° C. |
| 8 | Cl | Cl | —N= | benzyl | H | H | 148–150° C. |
| 9 | Cl | Cl | —CH= | allyl | H | H | 144–146° C. |
| 10 | Cl | Cl | —N= | allyl | H | H | oil |
| 11 | CF$_3$ | NO$_2$ | —CH= | allyl | H | H | 59–61° C. |
| 12 | CF$_3$ | NO$_2$ | —CH= | n-butyl | phenyl | phenyl | 129–131° C. |
| 13 | CF$_3$ | NO$_2$ | —CH= | benzyl | phenyl | phenyl | 85–87° C. |
| 14 | Cl | Cl | —N= | benzyl | phenyl | phenyl | 57–61° C. |

EXAMPLES 15–32

The following compounds of formula I were prepared by methods analogous to that of Example 2:

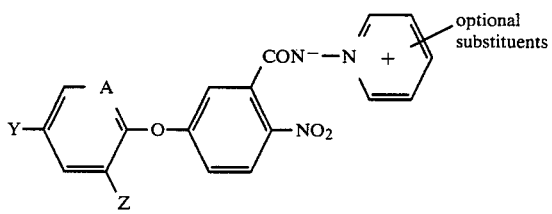

| Ex No. | Y | Z | A | Optional substituents | mpt |
|---|---|---|---|---|---|
| 15 | Cl | Cl | —CH= | — | 199–201° C. |
| 16 | Cl | Cl | —CH= | 2-methyl | 159–162° C. |
| 17 | Cl | Cl | —N= | — | 215–217° C. |
| 18 | Cl | Cl | —CH= | 3-methyl | 143–145° C. |
| 19 | Cl | Cl | —N= | 3-methyl | 183–185° C. |
| 20 | Cl | Cl | —CH= | 4-ethyl | 123–126° C. |
| 21 | Cl | Cl | —CH= | 2-ethyl | 181–183° C. |
| 22 | Cl | Cl | —CH= | 2-methyl,5-ethyl | 103–104° C. |
| 23 | Cl | Cl | —CH= | 3,5-dimethyl | 180–182° C. |
| 24 | Cl | Cl | —CH= | 3,4-(—CH=CH—CH=CH—) | 233–235° C. |
| 25 | CF$_3$ | Cl | —CH= | 3-methyl | 133–134° C. |
| 26 | CF$_3$ | Cl | —CH= | 4-ethyl | 136–138° C. |
| 27 | CF$_3$ | Cl | —CH= | 3,5-dimethyl | 167–169° C. |
| 28 | CF$_3$ | Cl | —CH= | 2-methyl,5-ethyl | 110–112° C. |
| 29 | CF$_3$ | Cl | —CH= | 3,4-(—CH=CH—CH=CH—) | 198–199° C. |
| 30 | CF$_3$ | Cl | —CH= | 2-ethyl | 154–155° C. |

-continued

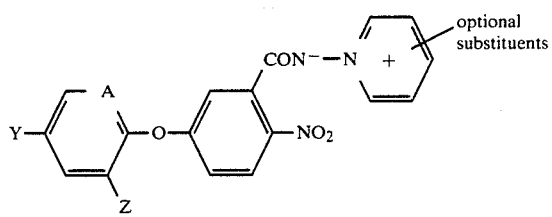

| Ex No. | Y | Z | A | Optional substituents | mpt |
|---|---|---|---|---|---|
| 31 | CF₃ | NO₂ | —CH= | 3-methyl | 204–206° C. |
| 32 | CF₃ | NO₂ | —CH= | — | 160–161° C. | effect, 4=severe effect and 5=complete kill. The results obtained were as follows:

| Compound | Ex No. | | | | | | | | | | | | | | | |
|---|---|---|---|---|---|---|---|---|---|---|---|---|---|---|---|---|
| | 1 | 2 | 3 | 4 | 5 | 6 | 9 | 10 | 11 | 14 | 15 | 16 | 18 | 19 | 25 | 32 |
| Setaria viridis | 5 | 5 | 5 | 5 | 4 | 2 | 3 | 2 | 4 | 4 | 5 | 5 | 5 | 5 | 5 | 5 |
| Stellaria media | 4 | 5 | 5 | 3 | 4 | — | — | — | — | — | — | — | — | — | — | — |
| Galium aparine | 5 | 5 | 5 | 5 | 4 | 4 | 3 | 3 | 4 | 3 | 4 | 4 | 5 | 4 | 5 | 4 |
| Chrysanthemum segetum | 5 | 5 | 5 | 5 | 4 | 4 | 2 | 2 | 3 | 5 | 4 | 5 | 4 | 3 | 5 | 4 |
| Abutilon theophrasti | 5 | 5 | 5 | 5 | 5 | 3 | 4 | 4 | 3 | 5 | 3 | 4 | 4 | 3 | 5 | 4 |
| Ipomoea annua | 5 | 5 | 5 | 4 | 4 | 3 | 2 | 2 | 2 | 4 | 3 | 4 | 3 | 2 | 4 | 3 |
| Xanthium pungens | 5 | 4 | 5 | 4 | 5 | 3 | 2 | 1 | 2 | 2 | 2 | 4 | 4 | 2 | 4 | 3 |
| Alopecurus myosuroides | 5 | 5 | 5 | 5 | 4 | 1 | 2 | 2 | 1 | 3 | 4 | 3 | 2 | 1 | 5 | 4 |
| Avena fatua | 5 | 5 | 5 | 5 | 3 | 1 | 1 | 2 | 2 | 2 | 1 | 3 | 2 | 2 | 5 | 3 |
| Agropyron repens | 4 | 5 | 5 | 5 | 3 | 3 | 1 | 1 | 2 | 1 | 2 | 2 | 2 | 1 | 3 | 4 |
| Echinochloa crus-galli | 5 | 5 | 5 | 5 | 4 | 2 | 2 | 2 | 2 | 3 | 1 | 2 | 1 | 1 | 3 | 4 |
| Cyperus rotundus | 4 | 4 | 4 | 3 | 2 | — | — | — | — | — | — | — | — | — | — | — |

EXAMPLE A

Seeds of the plant species listed below were sown in anodised aluminium pans, 19 cm long×9.5 cm wide containing sterilised sandy loam. They were then watered and placed in a controlled environment room (22° C.; 65–86% relative humidity; 14 hours per day artificial illumination, at 13,000 lux). Fourteen or twenty-one days after sowing (depending on the species but when most plants had 2 to 3 true leaves) the seedlings received a foliar spray of the compounds listed below, formulated as a solution in 1:1 by volume of acetone and the wetting agent polyoxyethylene (20 mols) monolaurate solution (10 g per liter).

The concentration of each test compound was calculated to give the desired rate of application (2.5 kg/ha) of the compound in 450 liters per hectare. After 21 days growth in the controlled environment room the plants were visually assessed for any herbicidal response.

All differences from an untreated control were scored according to an index where 0=no effect, 1=very slight effect, 2=slight effect, 3=moderate

EXAMPLE B

Seeds of the plant species listed below were sown in trays (19 cm×9.5 cm×6 cm) on top of a layer of sterilised loam (4.5 cm deep), and were covered with a further thin layer (5 mm) of loam. Each tray was then sprayed with a solution of one of the test compounds listed below, at a rate sufficient to give a dose equivalent to 2.5 kg/ha. A further layer of loam (5 mm) was then applied to each tray.

The trays were then watered and placed in a controlled environment room (20° C.; 75–95% relative humidity; 14 hours per day artificial illumination, at 13,000 lux) for 21 days. The plants were then visually assessed for any herbicidal or growth regulant effects. All differences from an untreated control were scored according to an index where 0=no effect, 1=very slight effect, 2=slight effect, 3=moderate effect, 4=severe effect and 5=complete kill.

The results are shown in the following table:

| Compound | Ex No | | | | | | | | | | | | |
|---|---|---|---|---|---|---|---|---|---|---|---|---|---|
| | 1 | 2 | 3 | 4 | 5 | 6 | 8 | 11 | 15 | 16 | 17 | 18 | 25 | 32 |
| Setaria viridis | 5 | 5 | 5 | 5 | 5 | 4 | 3 | 5 | 5 | 5 | 4 | 4 | 4 | 5 |
| Stellaria media | 5 | 5 | 5 | 5 | 2 | — | — | — | — | — | — | — | — | — |

-continued

| Compound | 1 | 2 | 3 | 4 | 5 | 6 | 8 | 11 | 15 | 16 | 17 | 18 | 25 | 32 |
|---|---|---|---|---|---|---|---|---|---|---|---|---|---|---|
| Galium aparine | 5 | 5 | 5 | 5 | 5 | 2 | 3 | 3 | 5 | 4 | 3 | 2 | 5 | 5 |
| Chrysanthemum segetum | 5 | 5 | 5 | 5 | 5 | 5 | 5 | 5 | 5 | 5 | 5 | 5 | 5 | 5 |
| Abutilon theophrasti | 5 | 5 | 5 | 5 | 5 | 5 | 5 | 5 | 5 | 5 | 1 | 5 | 5 | 4 |
| Ipomoea annua | 5 | 5 | 5 | 5 | 5 | 2 | 3 | 0 | 4 | 0 | 1 | 3 | 4 | 2 |
| Xanthium Pungens | 5 | 5 | 5 | 5 | 5 | 5 | 0 | 1 | 4 | 2 | 4 | 2 | 5 | 4 |
| Alopecurus myosuroides | 5 | 5 | 5 | 5 | 4 | 3 | 1 | 3 | 5 | 4 | 4 | 4 | 5 | 5 |
| Avena fatua | 5 | 5 | 5 | 5 | 3 | 1 | 1 | 0 | 5 | 3 | 1 | 3 | 4 | 4 |
| Agropyron repens | 5 | 5 | 5 | 5 | 3 | 1 | 1 | 2 | 2 | 0 | 4 | 3 | 4 | 4 |
| Echinochloa crus-galli | 5 | 5 | 5 | 5 | 5 | 0 | 0 | 0 | 5 | 4 | 2 | 4 | 5 | 5 |
| Cyperus rotundus | 4 | 4 | 3 | 3 | 0 | 0 | — | — | — | — | — | — | — | — |

EXAMPLE C

A 25% wettable powder formulation was prepared by mixing and micronising together the following ingredients:

| | |
|---|---|
| Compound of Example 1 | 25% by weight |
| Arkopon T high conc. (sodium oleoyl N—methyltauride) | 5% by weight |
| HOE S-1998 (30% isotridecyl alcohol + 8 moles ethylene oxide on silica) | 5% by weight |
| China clay | to 100% |

EXAMPLE D

A 25% wettable power formulation was prepared by mixing and micronising together the following ingredients:

| | |
|---|---|
| Compound of Example 2 | 25% by weight |
| Reax 45L (sodium lignosulphonate) | 5% by weight |
| China clay | 70% by weight |

I claim:

1. A compound of the formula:

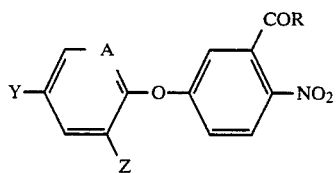 (I)

where
Y represents halo or trifluoromethyl;
Z represents hydrogen, halo, trifluoromethyl or nitro;
A represents —N= or

where X is as defined above for Z; and
R represents —N⁻Q⁺ or —NH—Q⁺An⁻ where Q⁺ is a pyridinium bonded through a nitrogen atom thereof, and An⁻ is a suitable anion.

2. A compound according to claim 1 wherein A represents

and one of X and Z, but not both, represents hydrogen.

3. A compound according to claim 1 wherein Y represents trifluoromethyl, Z represents chloro, A represents —CH=, and R represents —N⁻Q⁺ where Q⁺ represents pyridinium-1-yl which may be substituted on one or more of its carbon atoms.

4. A compound according to claim 1 wherein Q⁺ represents unsubstituted pyridinium-1-yl.

5. The compound according to claim 1 wherein Q⁺ represents pyridinium-1-yl.

6. 5-(2-chloro-4-trifluoromethylphenoxy)-N-(4-ethyl-1-pyridinio)-2-nitrobenzamidate.

7. 1-[5-(2-chloro-4-trifluoromethylphenoxy)-2-nitrobenzamido]pyridinium internal salt.

8. A herbicidal composition which comprises from 0.5 to 99% by weight of one compound according to claim 1 in association with a suitable surface active agent and/or a carrier.

9. The herbicidal composition according to claim 8 wherein Q⁺ represents pyridinium-1-yl.

10. The herbicidal composition according to claim 9 wherein A represents

and 1 of X and Z, but not both, represents hydrogen.

11. The herbicidal composition according to claim 8 wherein Y represents trifluoromethyl, Z represents chloro, A represents —CH=, and R represents —N⁻Q⁺ where Q⁺ represents pyridinium-1-yl which may be substituted on one or more of its carbon atoms.

12. The herbicidal composition according to claim 11 wherein Q⁺ represents unsubstituted pyridinium-1-yl.

13. The herbicidal composition according to claim 8 wherein the compound is 5-(2-chloro-4-trifluoromethylphenoxy)-N-(4-ethyl-1-pyridinio)-2-nitrobenzamidate.

14. The herbicidal composition according to claim 8 wherein the compound is 1-[5-(2-chloro-4-trifluoromethylphenoxy)-2-nitrobenzamido]pyridinium internal salt.

* * * * *